United States Patent [19]

Diesel

[11] 4,413,533
[45] Nov. 8, 1983

[54] SAMPLING DEVICE FOR ISOKINETIC SAMPLING

[75] Inventor: Hans A. Diesel, Annandale, N.J.

[73] Assignee: Exxon Research and Engineering Co., Florham Park, N.J.

[21] Appl. No.: 316,294

[22] Filed: Oct. 29, 1981

[51] Int. Cl.³ .............................................. G01N 1/20
[52] U.S. Cl. .............................. 73/863.31; 73/863.58; 73/863.86
[58] Field of Search ............ 73/863.31, 863.33, 863.58

[56] References Cited

U.S. PATENT DOCUMENTS

| | | | |
|---|---|---|---|
| 2,675,706 | 4/1954 | Edgar | 73/863.33 |
| 3,369,405 | 2/1968 | Galegar | 73/863.33 |
| 3,511,099 | 5/1970 | Harsha | 73/863.31 |
| 4,051,731 | 10/1977 | Bohl | |

FOREIGN PATENT DOCUMENTS

| | | |
|---|---|---|
| 2042227 | 3/1972 | Fed. Rep. of Germany . |
| 2327444 | 12/1974 | Fed. Rep. of Germany . |

OTHER PUBLICATIONS

"Fluid Dynamic Measurements in Air/Water Mixtures Using a Pitot Tube and Gamma Densitometer", J. R. Fincke/V. A. Deason, EG&G Idaho, Inc. (I.S.A. Transactions, vol. 19, No. 2, 1980).

*Primary Examiner*—S. Clement Swisher
*Attorney, Agent, or Firm*—Donald F. Wohlers

[57] ABSTRACT

A sampling device for isokinetic sampling of a flowable substance passing through a conduit comprises a plurality of relatively narrow tubes (27) of substantially equal length each open at one end and terminating in a metering valve (30) at the other end. The tubes (27) are sealed within an externally smooth sheath (28) and the open ends protrude different distances from the sheath, substantially along a straight line parallel to the axis of the sheath (28). The end portions of the tubes (27) are parallel to each other and perpendicular to the sheath's axis so as to be substantially parallel to the axis of the conduit, when disposed for use. The open ends of the tubes (27) are substantially in a common plane perpendicular to the lengths of the end portions. The other ends of the tubes are connected to the metering valves which are calibratable for isokinetic sampling by means of calibration indicators (31), and the metering valves (30) are each connected to discharge valves (32) which are ganged together so as to be opened and shut simultaneously by the movement of a hinged operating bar (37). When the metering valves (30) are correctly set, movement of the operating bar (37) enables flowable substance to pass isokinetically through respective tubes (27) and discharge valves (32) when the latter are opened to provide a corresponding number of simultaneous isokinetic samples of flowable substance. A sample homogenization device (FIG. 7) provides for mixing of collected samples (usually about 1 liter samples) prior to laboratory analysis.

15 Claims, 12 Drawing Figures

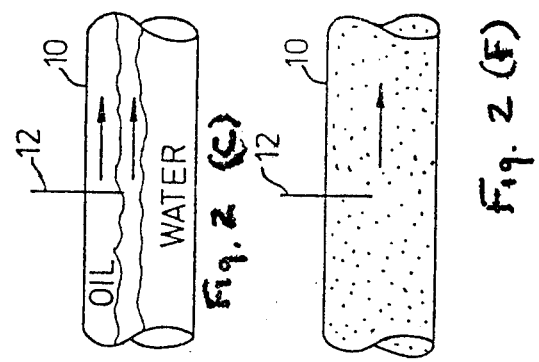
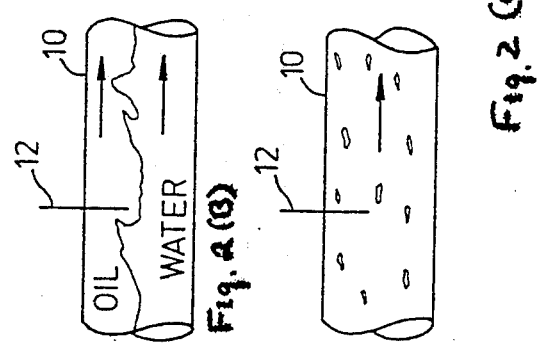
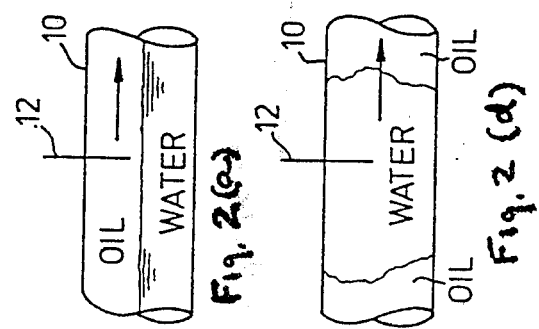

SAMPLING DEVICE FOR ISOKINETIC SAMPLING

CROSS REFERENCE TO RELATED APPLICATIONS

This application is a substitute for previously abandoned U.S. Ser. No. 166,903 filed July 8, 1980.

The present invention relates to a sampling device for isokinetic sampling of a flowable substance passing through a conduit.

In many industries, it is important to know the quality and/or composition of a stream of flowable substance passing through a conduit in order to make appropriate adjustments to correct or compensate for such a stream when its quality and/or composition deviates from a desired value. Such an "appropriate adjustment" may be an adjustment to the price of the substance and/or to the means by which the substance is supplied and/or generated.

One method for monitoring the quality and/or composition of flowable substances passing through a conduit is to have installed partly in the conduit a sampler which has a single sampling port within the conduit from which samples of substances are delivered to a discharge port outside the conduit. The sampler may be of the type which delivers samples at a rate related to the rate of flow of the substance through the conduit. Such samplers have a sampling port which is usually of very small cross-sectional area compared to the cross-sectional area of the conduit, and thus gives rise to actual or potential problems in ascertaining whether the samples delivered from the sampler are truly representative of the substance flowing in the conduit.

It is an object of the present invention to provide a way of checking on whether a sampler is or is not furnishing representative samples so that adjustments to the sampler, the samples or oth er factors may be made to improve the accuracy of sampling.

The present invention provides a sampling device for sampling a flowable substance passing through a conduit comprising a plurality of tubes fixedly located relative to each other, each tube comprising an inlet end having an inlet opening, a discharge end having a discharge opening, and an operating valve for permitting and preventing flow through the tube, the volume contained in the tube between the inlet opening and the valve being substantially equal to the corresponding volume of each of the other tubes, the inlet openings of the tubes being spaced apart substantially in a common plane and facing in the same direction, and the device being so constructed and/or arranged for a part thereof including said inlet openings to be received in leakproof fashion through an orifice in the wall of the conduit, the device comprising operating means operable for opening and closing all said operating valves simultaneously and for regulating the flow rate through each tube when the respective operating valve is open.

Preferably, the regulation of flow rate through each tube is effected by a respective adjustable metering valve, and preferably, the metering valves are adjusted to provide substantially isokinetic sampling via the tubes when the operating valves thereof are open. Since the flow of substances through conduits in industry is generally turbulent, isokinetic flow through the tubes will be a rate of flow which is equal in all the tubes and determined by multiplying the ratio of the cross-sectional flow area of each tube to the cross-sectional area of the conduit by the rate of flow through the conduit. For flow other than turbulent flow, it is within the ability of the technologist in this field to calculate or determine by known methods the flow for each tube and to adjust the metering valves to obtain such flow so that isokinetic sampling of the substance in the conduit is effected.

The tubes are preferably fixedly located for at least part of their lengths between their inlet ends and their operating valves in an externally smooth hollow sheath which is insertable through the orifice in the conduit wall. Preferably, the sheath is substantially straight and provided with means for attachment of the sheath substantially radially with respect to the axis of the conduit.

The inlet ends of the tubes are preferably formed with their axes parallel to each other and substantially perpendicular to the said common plane. It is preferred that the inlet ends of the tubes are streamlined substantially to avoid disturbing the flow in the conduit at least in the immediate vicinity of each of the inlet openings.

The device preferably comprises means for aligning the inlet openings to be in a plane substantially perpendicular to the axis of the conduit.

The invention further provides an installation comprising the combination of a conduit for the flow of a substance in one direction therethrough, a permanent sampler having one end open within the conduit and the other end outside the conduit and means operable to cause the delivery of samples of flowable substance from said one end within the conduit to said other end outside the conduit, and a sampling device as described above sealingly received through the orifice in the conduit wall with the inlet ends of the device facing in a direction opposite to said one direction.

The permanent sampler may be a sampler of the type described in relation to the prior art, but whether it is or not, the sampler may be operable to deliver discrete samples intermittently, and preferably at a rate dependent on the flow-rate of flowable substance through the conduit.

The invention also provides a method of sampling a flowable substance passing in one direction through a conduit comprising disposing a sampling device as described above with its inlet ends within the conduit and facing in a direction opposite to the direction of flow of the flowable substance, operating said operating means so as to permit or cause flowable substance to pass simultaneously through the tubes, and recovering samples of flowable substance from the outlet openings of said tubes.

In order to determine, or to determine with increased accuracy, whether or not the samples delivered by the permanent sampler are representative of the substance flowing in the conduit, a contaminant may be passed at a known rate into the conduit at a location upstream of the sampling device, which is preferably upstream of the permanent sampler, and the distribution of the contaminant in the samples obtained from the tubes of the sampling device may be determined for comparison with the amount of contaminant in the samples delivered by the permanent sampler. The contaminant may be passed into the conduit at least at one other known rate so that comparisons of the amounts of contaminants in the samples from the tubes of the sampling device with the amounts of contaminants in the samples from the permanent sampler can be made to determine whether or not the samples from the latter are affected by the concentration of contaminant in the substance flowing through the conduit. It is preferred that the contaminant be one which is sometimes or always present in the substance.

The said operating means is preferably operated for a selected time and the flow rate through each metering valve is preferably so adjusted that the amount of each sample obtained from each tube is substantially proportional to the local flow rate of the substance at the inlet opening of the respective tube from which the sample is received.

Preferably, the composition of each sample (or a portion thereof) from each tube of the sampling device is determined, preferably after homogenizing the sample (or portion thereof). The sample (or portion) may be homogenized by passage in contact with a static mixing device. The invention further provides a sample mixer device to allow mixing and homogenization of collected samples prior to laboratory analysis. The position of this single sampling inlet of the permanent sampler is preferably so located that samples representative of the composition of the substance passing the location of the sampler, as determined from the samples received from the tubes of the sampling device, can be obtained. The said single inlet of the sampler may be at a fixed location lengthwise of the conduit, and the flow-rate and/or turbulence of flowable substance passing through the conduit is or are changed so that the sampler provides representative samples. Alternatively or in addition, the location of the single inlet of the sampler may be changed so that the sampler provides representative samples.

The invention is now further described by way of a non-limitative example thereof and with reference to the accompanying drawings in which:

FIG. 1 is a schematic drawing showing a method of and equipment for automatic crude oil sampling;

FIGS. 2A, 2B, 2C, 2D, 2E and 2F schematically show different regions and types of flow of crude oil and water in a pipeline;

Figure 1:
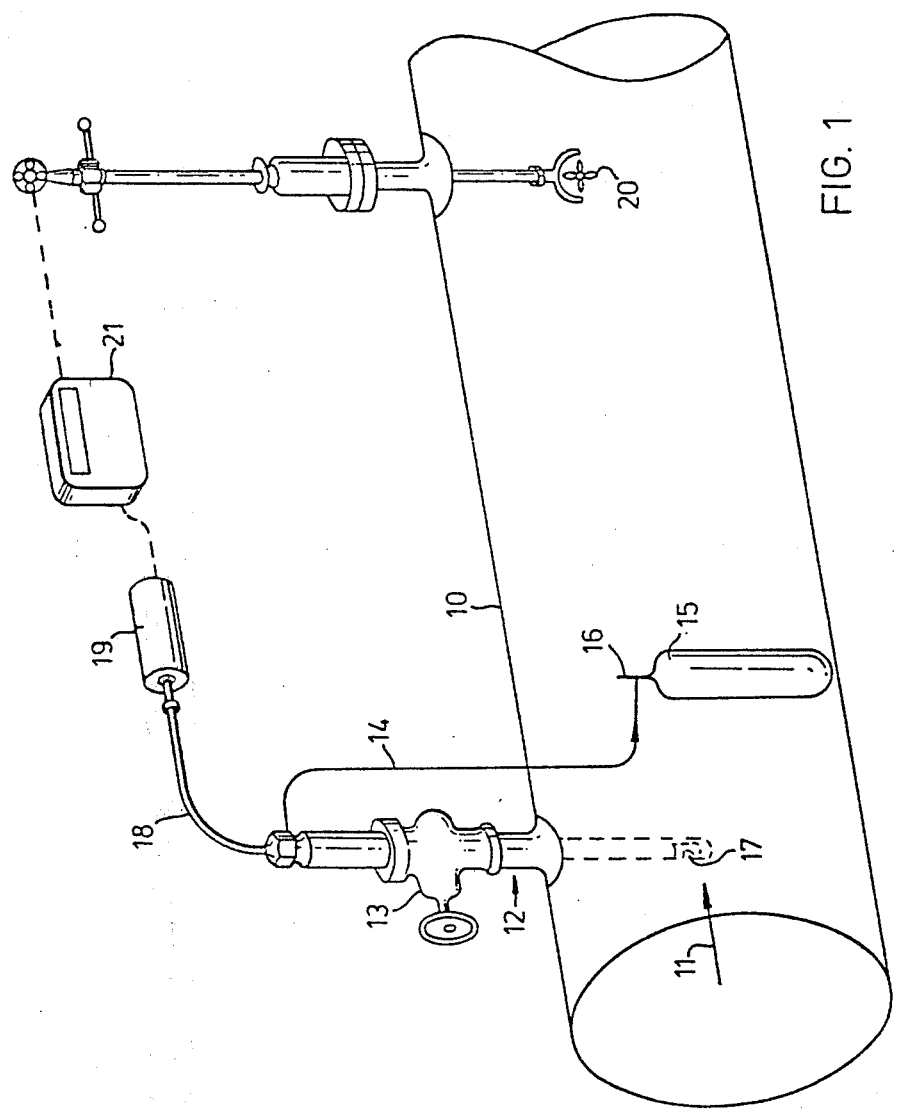

Referring first to FIG. 1, there is depicted schematically a typical arrangement of equipment for sampling crude oil which is passing through a pipeline. The pipeline is indicated by reference 10 and the direction of flow of the crude oil is indicated by arrow 11. A sampler 12 protrudes through a valve 13 and is connected by tube 14 to a sample receptacle 15 having an air vent 16. The sampler 12 has a single inletport 17 and comprises a rotatable valve (not shown) which can be rotated to close the port 17 and define a cylinder in which a sample of oil from port 17 is trapped, there being a cam operated piston which displaces the sample out of the cylinder into the tube 14. The rotation of the valve and cam are both effected by a flexible connection 18 from a suitable motor 19 (e.g. an air motor), and the speed of rotation is arranged to be proportional to the flow rate of oil, the latter being determined by a small turbine 20 which is rotated by the passage of oil and which transmits its rotation via suitable gearing and connections to a flow proportional controller 21 which controls the speed of the motor 19 so that it is proportional to the rotational speed of the turbine 20. Single port samplers 12 are commercially available from, for example, Clif Mock Company, Houston, Tex., U.S. and AOT Flowmeters Ltd., Andover, England, under the trade name "True-Cut."

Crude oil often contains contaminants, and the more important of these are water (often containing dissolved salts) and sediment (such as sand). If the crude oil is being pumped through the pipeline 10 from a storage tank (e.g. a cargo compartment of a marine tanker), the water and sediment content of the oil will vary depending on whether the oil is being pumped from the bottom of the tank, where water and sediment tend to accumulate to the greatest degree, or from elsewhere. Moreover, not only does the water and sediment content vary, but the degree and/or manner of its dispersion in the oil will vary depending on the amount of turbulence at particular locations in the pipeline 10. FIG. 2 shows a number of commonly-encountered situations for crude oil passing through the pipeline 10 and the manner in which the single port sampler 12 can provide misleading or inaccurate samples of the crude oil passing through the pipeline 10. In FIG. 2(a), the water forms a layer under the oil with the interface below the single inlet port (not indicated) at the bottom of the sampler 12. It can readily be appreciated that the sampler will provide samples in the receptacle 15 (FIG. 1) which are not at all representative of the oil-water mixture in the pipeline. The situation in FIG. 2(a) is most likely at very low pumping speeds. FIG. 2(b) depicts the situation at a higher pumping speed when the oil-water interface is disturbed by shearing, but it is apparent that the samples from sampler 12 will contain only a minor proportion of the actual water present in the pipeline 10. At a still higher flow rate, shown in FIG. 2(c), the water and oil at the interface are sheared to the extent that immediately below the top layer consisting of substantially water-free oil, is a mixture of oil and water, below which is a layer of substantially oil-free water. As shown in FIG. 2(c), the bottom of sampler 12 is too high to receive representative samples of the central oil-water layer, and even if it were lower, it would not necessarily receive oil-water samples truly representative of the mixture passing through the pipeline 12. FIG. 2(e) shows the greater and more uniform dispersion of water in the oil at still higher pumping rates, but the water tends to be in the form of relatively large lenses or globules which militate against accurate sampling by the sampler 12. FIG. 2(f) shows a regime in which the water is uniformly dispersed as small droplets suspended in the oil. In this regime, the samples from sampler 12 are likely to be substantially representative of the composition of the oil in the pipeline 10. It will be appreciated from the foregoing that the accuracy of sampling by the sampler 12 depends on the degree of turbulence of the oil as it approaches and passes the sampler 12 and also on the depth of insertion of the bottom of the sampler 12 into the pipeline 10. The turbulence is affected by the pumping rate, the configuration of the pipeline 10 and any turbulence-creating obstacles therein, inter alia, and the separation of the water from the oil can also be affected by the pumping machinery (e.g., centrifugal pumps tend to promote separation). FIG. 2(d) shows a plug of water passing through the pipeline 10. Such a plug can be accurately sampled if it is not so short that it passes the sampler 12 while its inlet port is closed.

Figure 3:
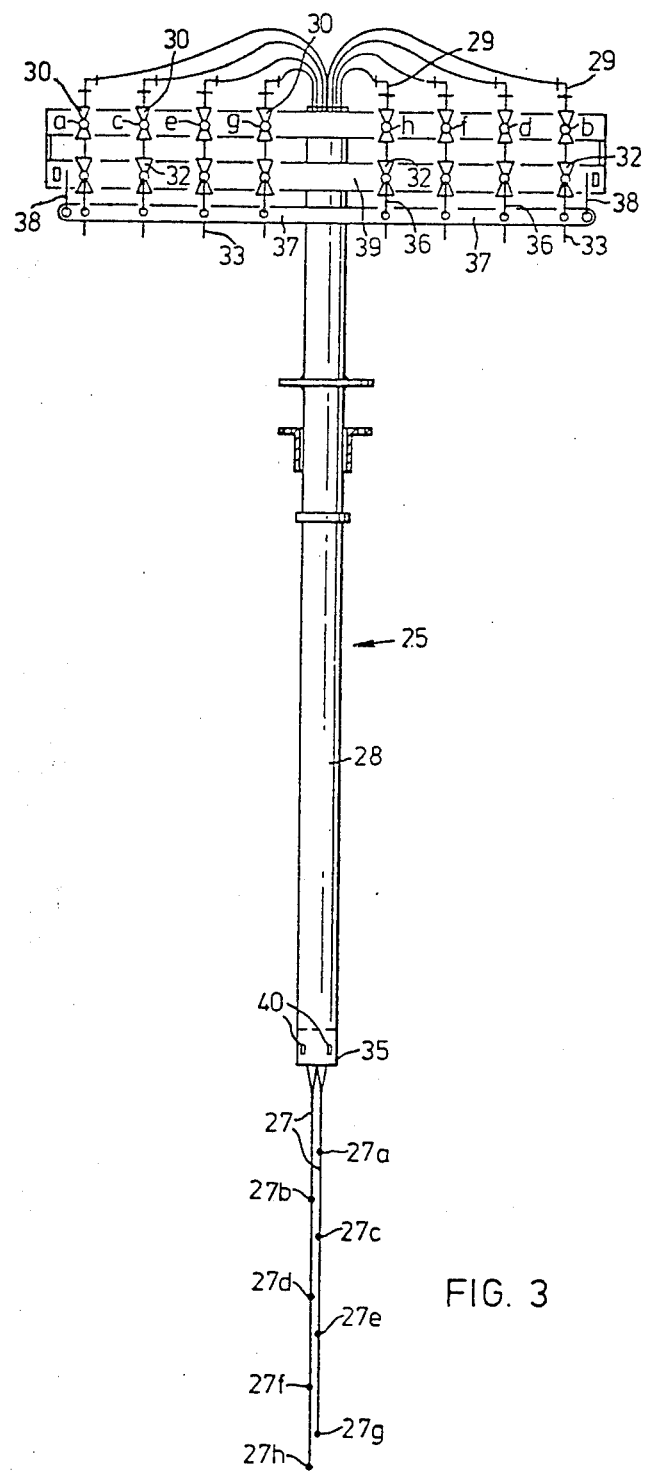
FIGS. 3 and 4 are respective diagrammatic front and side elevations of a sampling device of the invention.
Figure 4:
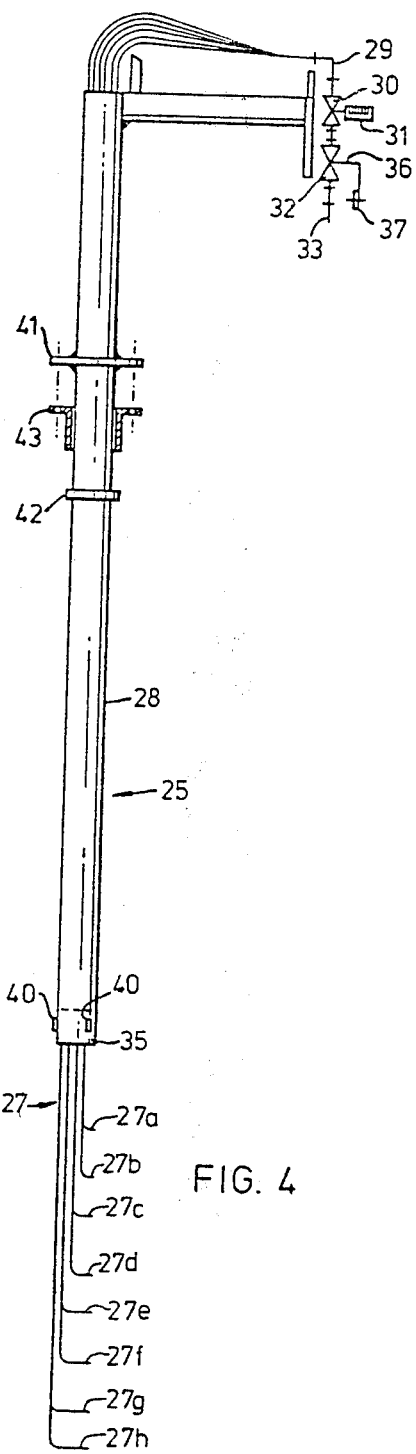

In order to ascertain whether or not the sampler 12 is installed in a position such that during operation, its single inlet port is at a position at which it will be able to receive and produce representative samples at flow conditions such as those described in relation to FIGS. 2(f) and 2(d), and also to ascertain whether or not flow conditions such as those described in relation to FIG. 2(f) are attained or attainable at the location of the sampler 12, a sampling device or probe 25 as described hereinafter, e.g. in relation to FIGS. 3 and 4 (inter alia), is installed in the pipeline 12. For a 24 inch (about 0.61 meter) diameter pipeline, the probe 25 may suitably be about 1 meter) upstream of the sampler 12.

As will be seen from FIGS. 3 and 4, the probe 25 comprises eight narrow tubes 27 fixedly received in, and sealed in, a hollow steel sheath 28 to different distances and have their end portions substantially perpendicular to the axis of the sheath 28 and their open ends substantially in a common plane. The tubes 27 protrude out of the top of the sheath 28 and each tube is connected to an elbow 29, a metering valve 30 with a valve-setting indicator 31, a discharge valve 32, and a discharge tube 33. The tubes 27 are all the same length and it is arranged that the tube 27 which extends downwards the least distance from the bottom of sheath 28 should extend the greatest distance out of the top of the sheath 28 before its connection to its elbow 29 and that the tube 27 which extends the greatest distance from the bottom of the sheath 28 should extend the least distance out of the top of the sheath 28 before connection to its respective elbow 29. As shown, there are eight tubes 27, and they are identified respectively as tubes 27a, b, c, d, e, f, g and h. Their respective metering valves are correspondingly identified by suffix letters.

As can be seen from FIG. 3, the open ends of the tubes 27 are arranged in two closely spaced lines within the envelope of the circumference of the sheath and parallel to the axis of the sheath 28, one line comprising tubes 27a, c, e and g and the other comprising tubes 27b, d, f and h. The end part of each tube is formed from $\frac{1}{4}$ inch (6.35 mm) stainless steel tube and the remaining part of the tube from 3/8 inch (9.375 mm) stainless steel tubing into which the end part is received and silver soldered. Preferably, the tips of the end parts are streamlined by forming them to a 45° chamfer around the open end. The open ends are so arranged that when the probe 25 is disposed for use with the open end of tube 27d on the central axis of the pipeline, the open ends of the other tubes are spaced from the axis of the pipeline by the following distances: 27a and 27g, 0.75R where R is the radius of the pipeline; 27b and 27f 0.5R; 27c and 27e 0.25R; and 27h 0.925R. Other spacings may be employed instead of the foregoing.

The tubes 27 are sealed in the sheath 28 by a silver solder plug 35.

The discharge valves 32 are each connected by a lug 36 to a plate 37 which is attached by hinges 38 at each end to a frame 39 on which the valves 30 and 32 are mounted. The weight of the plate 37 normally maintains the valves 32 closed and the arrangement is such that when the plate 37 is raised or lifted away from the frame 39, all of the valves 32 are opened simultaneously and closed simultaneously when the plate 37 is released. The valves 32 are preferably connected to plate 37 via respective toggle mechanism (not shown) so that they are each normally either fully open or fully closed.

Near the bottom of the sheath 28 and on the exterior are a plurality (e.g. 3) of equiangularly-located projections 40 (e.g. weld spots) filed to project the same distance from the surface of the sheath 28 to guide the sheath when the probe 25 is being emplaced for use. Near the top of the sheath 28, there is welded a locking flange 41 having arcuate slots (not shown) therein for receiving bolts and permitting a limited amount of rotational movement, and the flange 41 has one or more alignment marks thereon, one of which is parallel to, or less preferably at a known angle to, the out-turned bottom end parts of the tubes 27. A ring 42 is slidably disposed around the sheath 28 between the projections 40 and the locking flange 41, and a slidable gland ring 43 is disposed around the sheath 28 between the ring 42 and the locking flange 41.

Figure 5:
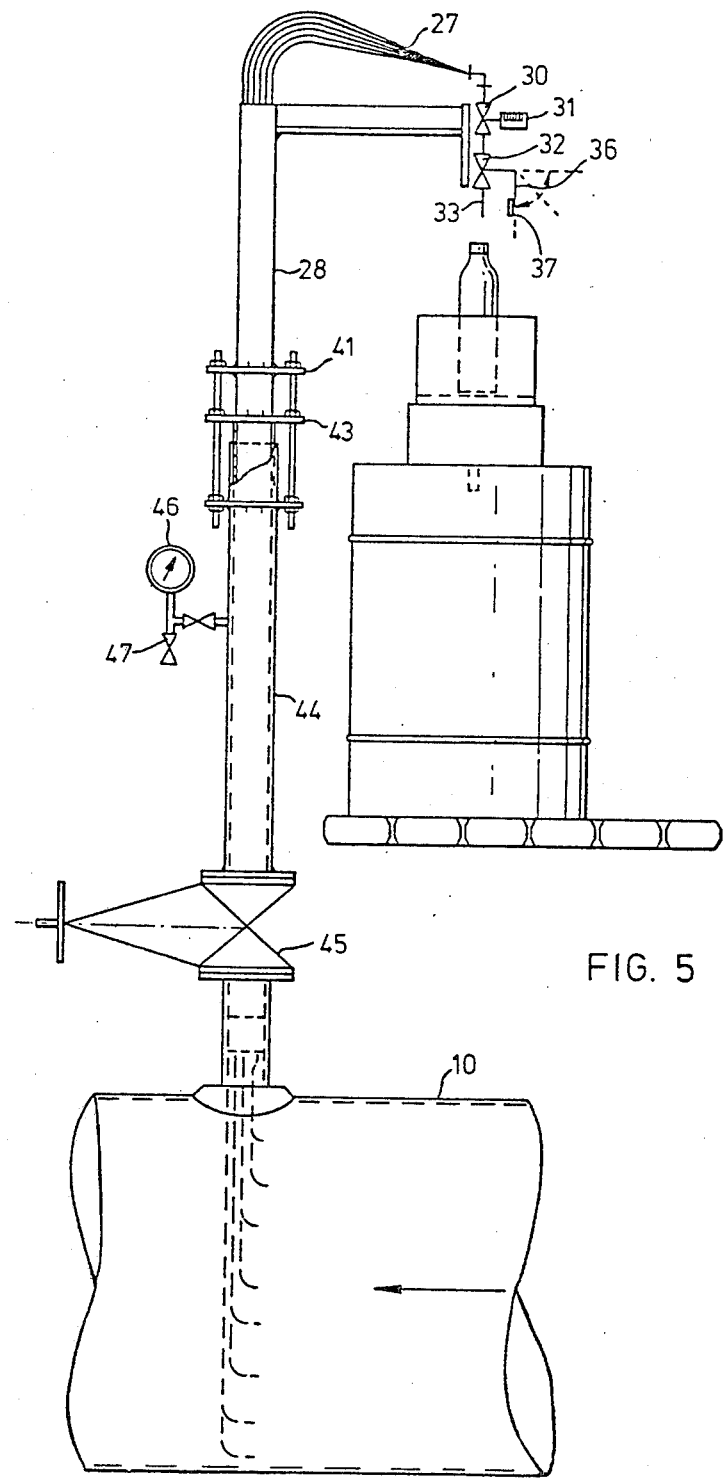
FIGS. 5 and 6 are respective diagrammatic side and front views of the sampling device emplaced for use.
Figure 6:
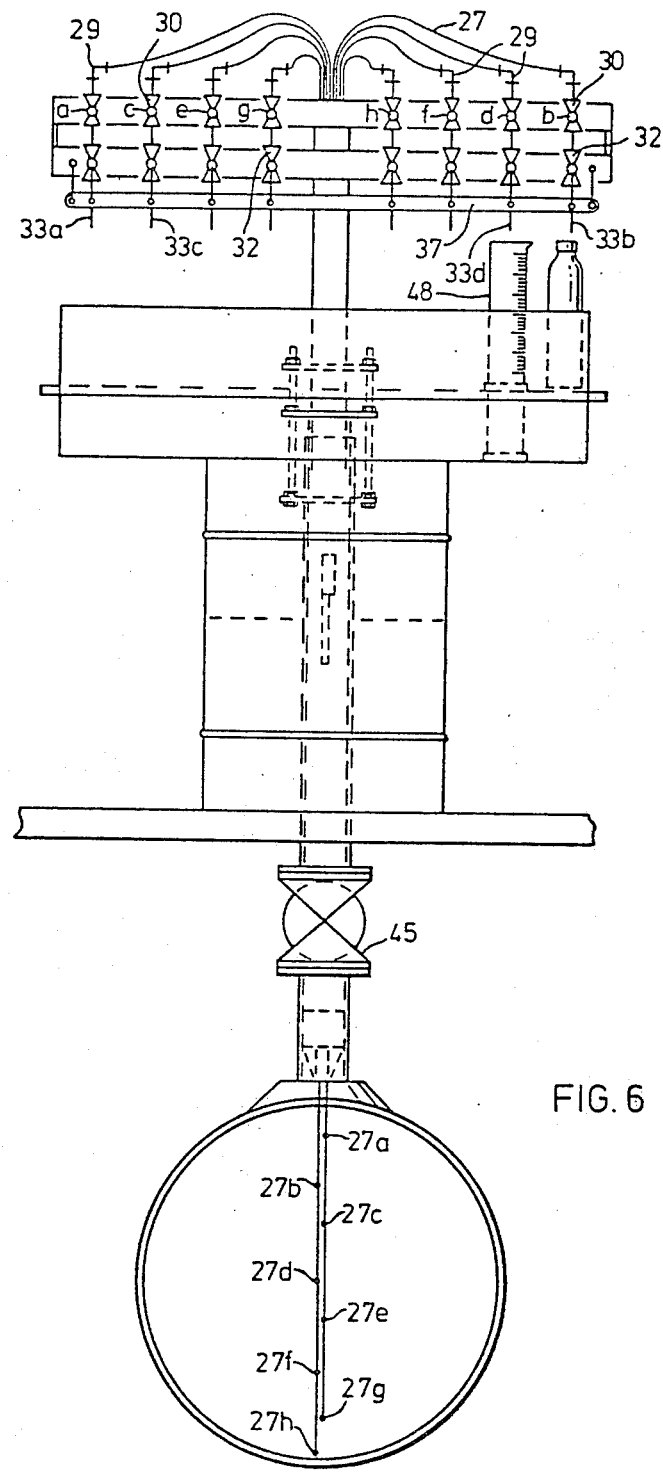

Reference is now made to FIGS. 5 and 6 which show the probe emplaced in the pipeline 10 and ready for use.

The sheath 28 is passed down a vertical standpipe 44 until the tube 27d has its open end on the axis of the pipe. The standpipe 44 comprises a full bore gate valve 45 for inserting the probe 25 into the pipeline 10, and the top of the standpipe is closed by the engagement of the sliding ring 42 and gland ring 43 between the sheath 28 and the inner surface of the top of the standpipe 44, and the angular disposition of the probe relative to the axis of the pipeline is set by aligning one or more marks on flange 41 with corresponding marks (not shown) on the standpipe or some other part which is fixed relative to the axis of the pipeline. The standpipe 44 is furnished with a pressure gauge 46 and a drain valve 47.

The probe 25 is calibrated by calculating the volume flow rate through the tubes 27 taking into account the volume flow rate through the pipeline 10 and the internal cross-sectional flow area of the pipeline 10. As shown in FIG. 6, a measuring cylinder 48 is placed under discharge 33d with the valves 30 for the other discharge tubes 33 closed, and the metering valve 30d is adjusted until the correct flow rate for the tube 27d is obtained. The setting of the valve 30d, as indicated by indicator 31d, is then applied to all of the other metering valves so that on raising the plate 37, all of the tubes 27 deliver crude oil at the same rate (within acceptable limits of error) appropriate to the minimum flow area of the tubes and the flow rate in the pipeline 10.

When the probe 25 has been calibrated, suitable clean receptacles are disposed beneath each discharge tube 33, labelled to indicate which tube they are to receive liquid from, and the plate 37 is lifted for a predetermined time or until a predetermined amount of liquid is discharged into each receptacle.

Figure 7:
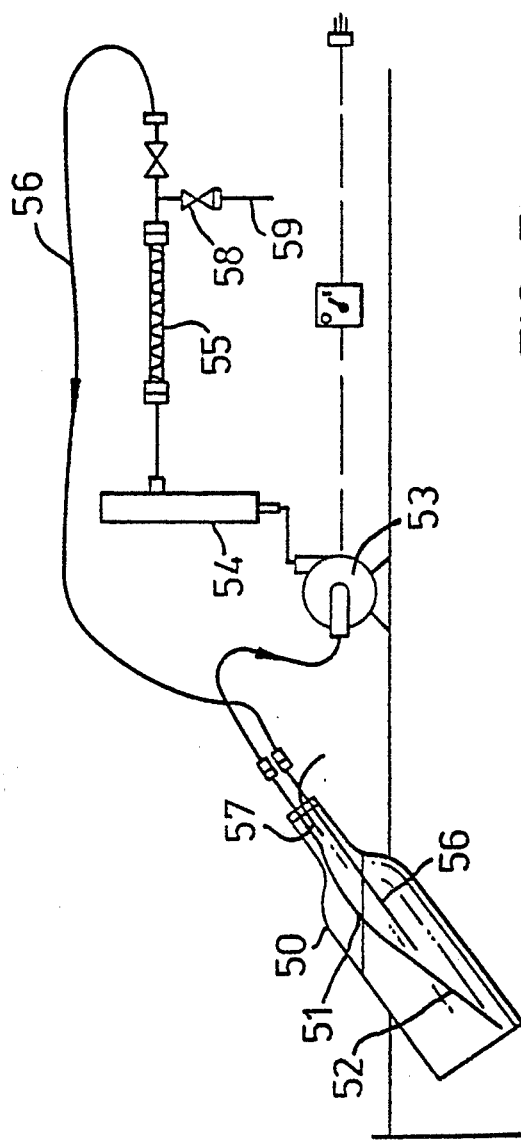
FIG. 7 is a schematic diagram of equipment for homogenizing the samples obtained by use of the sampling device, and which is also a part of the invention.

Each receptacle is removed and its contents are then homogenized in its respective receptacle. Preferably, the homogenization is effected employing the equipment shown schematically in FIG. 7. The receptacle 50 containing its sample is connected to a sample circulation loop comprising an offtake tube 51 having an orifice 52 in its side, a circulation pump 53, a flowmeter 54 (e.g. of the variable-area type such as a rotameter, an in-line static mixer 55 (such as that available under the trade name Kenics) and a return tube 56. The receptacle is vented via an open tube 57. After the sample has been circulated for a predetermined time, valve 58 is opened to purge residual material via tube 59 from previous tests using some of the homogenized sample, and then some of the sample is recovered for analysis via valve 58 and tube 59. The analysis for water and sediment is performed according to any suitable standard method, e.g. ASTM D96-73 (primary method). The analyses for the samples from each tube should be the same within acceptable limits of error. If the analyses are not the same within the limits of error, the sampling effected by the single inlet sampler 12 of FIGS. 1 and 2 is not likely to be representative of the composition of the oil passing through the pipeline 10 and expedients to improve this must be adopted. These expedients comprise increasing the oil flow rate, locating the sampler 12 at a position where turbulence is greater, disposing in the pipeline upstream of the sampler 12 suitable means to create turbulence to provide substantial uniformity of dispersion of water and sediment.

If the procedure described proves to be satisfactory, investigations are preferably conducted to establish that the sampler 12, in its existing or new location, or with any of the other expedients for improving uniformity of dispersion alone or in combination in use, provides satisfactorily representative sampling under a number of "worst case" conditions. A typical worst case condition is when the crude oil is a light crude oil having a high water (or other contaminant) content. To this end, water is passed into the pipeline 10 at a location well upstream of the probe 25 and sampler 12 when a light crude oil is being pumped therethrough. The foregoing operations are repeated and the compositions of the samples collected from the probe should give the same analysis within the limits of error. Moreover, it should be possible to correlate the water in the analysed samples with the amount of water injected and thereby obtain a water balance. The procedure is repeated with progressively higher concentrations of water (provided by water injection) until at water concentrations corresponding to the highest likely to be met in day-to-day operations, the compositions of the homogenized samples obtained via the probe 25 are the same within the acceptable limits of error, and enable an acceptable water balance to be calculated. If, in the latter case, acceptable results are obtained, the sampler 12 may be regarded as providing representative samples.

I claim:

1. A sampling device for isokinetic sampling of a flowable substance passing through a conduit comprising a plurality of tubes fixedly located relative to each other, each tube including an inlet end having an inlet opening, a discharge end having a discharge opening, an adjustable metering valve means for regulating the flow rate through each tube and an operating valve for permitting and preventing flow through each tube, the volume contained in each tube between the inlet opening and the valve being substantially equal to the corresponding volume of each of the other tubes, the inlet openings of the tubes being spaced apart substantially in a common plane and facing in the same direction, and the sampling device being so constructed and arranged for a part thereof including said inlet openings to be received in leak-proof fashion through an orifice in the wall of the conduit, operating plate means connected to each said operating valve for opening and closing all said operating valves simultaneously when each said separate metering valve means has been set to substantially equalize the flow rate through each tube, and a plurality of individual containers located adjacent each said tube discharge end to receive a plurality of individual samples therein upon opening of each said operating valve means.

2. A device as in claim 1 in which the tubes are fixedly located for at least part of their lengths between their inlet ends and their operating valves in an externally smooth hollow sheath which is insertable through the orifice in the conduit wall.

3. A device as in claim 2 in which the said sheath is substantially straight and provided with means for attachment of the sheath substantially radially with respect to the axis of the conduit.

4. A device as in claim 3 in which the inlet ends of the tubes are formed with their axes parallel to each other and substantially perpendicular to the said common plane.

5. A device as in claim 4 in which the inlet ends of the tubes are streamlined.

6. A device as in claim 5 comprising means for aligning the inlet openings to be in a plane substantially perpendicular to the axis of the conduit.

7. A sampling installation comprising the combination of a conduit for the flow of a substance in one direction therethrough, a permanent conventional single point sample having one end open within the conduit and the other end outside the conduit and means operable to cause the delivery of individual samples of flowable substance for analysis from said one end within the conduit to said other end outside the conduit, and an upstream sampling device for verification of said conventional sampler according to claim 1 sealingly received through the orifice in the conduit wall with the inlet ends of the device facing in a direction opposite to said one direction.

8. An installation according to claim 7 in which conventional sampler is operable to deliver discrete samples intermittently.

9. An installation according to claim 8 in which the permanent sampler is operable to deliver discrete samples at a rate dependent on the flow-rate of flowable substance through the conduit.

10. A method of sampling a flowable substance passing in one direction through a conduit comprising disposing a sampling device according to claim 1 with the inlet ends of each tube within the conduit facing in a direction opposite to said one direction, operating said operating plate means so as to permit or cause flowable substance to pass simultaneously through the tubes, and recovering samples of flowable substance in individual containers from the outlet openings of each said tube.

11. A method as in claim 10 comprising passing a contaminant at a known rate into the conduit at a location upstream of the sampling device, homogenizing each collected sample, and analyzing each separate collected sample to determine the distribution of the contaminant in the flowable substance.

12. A method as in claim 11 comprising passing the contaminant into the conduit at said location at least at one other known rate, and determining its distribution in the flowable substance from at least one other set of samples.

13. A method as in claim 12 in which said operating means is operated for a selected time and the flow rate through each metering valve is so adjusted that the amount of each sample obtained from each tube is substantially proportional to the local flow rate of the substance at the inlet opening of the respective tube from which the sample is received.

14. A method as in claim 13 in which a conventional sampler operates to provide samples of substance outside the conduit from a single sampling inlet inside the conduit is so located that the sample inlet is at a position from which samples representative of the composition of the substance passing the location of the sampler, as determined from the samples received from the tubes of the sampling device, can be obtained.

15. A method as in claim 14 in which the single inlet of the sampler is at a fixed location lengthwise of the conduit, and the flow rate and turbulence of flowable substance passing through the conduit and the location of the sampler inlet is changed so that the sampler provides representative samples.

* * * * *